United States Patent
Wei

(10) Patent No.: US 8,258,320 B2
(45) Date of Patent: Sep. 4, 2012

(54) N ALKYLCARBONYL AMINO LACTONE COMPOUNDS AND THEIR USE

(76) Inventor: Edward Tak Wei, Berkeley, CA (US)

( * ) Notice: Subject to any disclaimer, the term of this patent is extended or adjusted under 35 U.S.C. 154(b) by 2 days.

(21) Appl. No.: 12/930,801

(22) Filed: Jan. 18, 2011

(65) Prior Publication Data

US 2012/0184608 A1   Jul. 19, 2012

Related U.S. Application Data

(63) Continuation-in-part of application No. 11/910,185, filed on Sep. 28, 2007, now abandoned.

(51) Int. Cl.
*C07D 321/00* (2006.01)
(52) U.S. Cl. .................................................. 549/321
(58) Field of Classification Search .................. 549/321
See application file for complete search history.

*Primary Examiner* — Nizal Chandrakumar

(57) ABSTRACT

The present invention generally relates to refreshing, soothing, and cooling compounds that affect sensory processes. More particularly, the present invention pertains to certain N-alkylcarbonyl-amino lactone compounds as described herein; compositions and articles comprising such compounds; and methods of treatment, for example, methods of alleviating the discomforts of irritation, itch, and pain in the skin and in the linings of the oral cavity and upper respiratory tract, for example, in methods of treatment of cough.

7 Claims, 1 Drawing Sheet

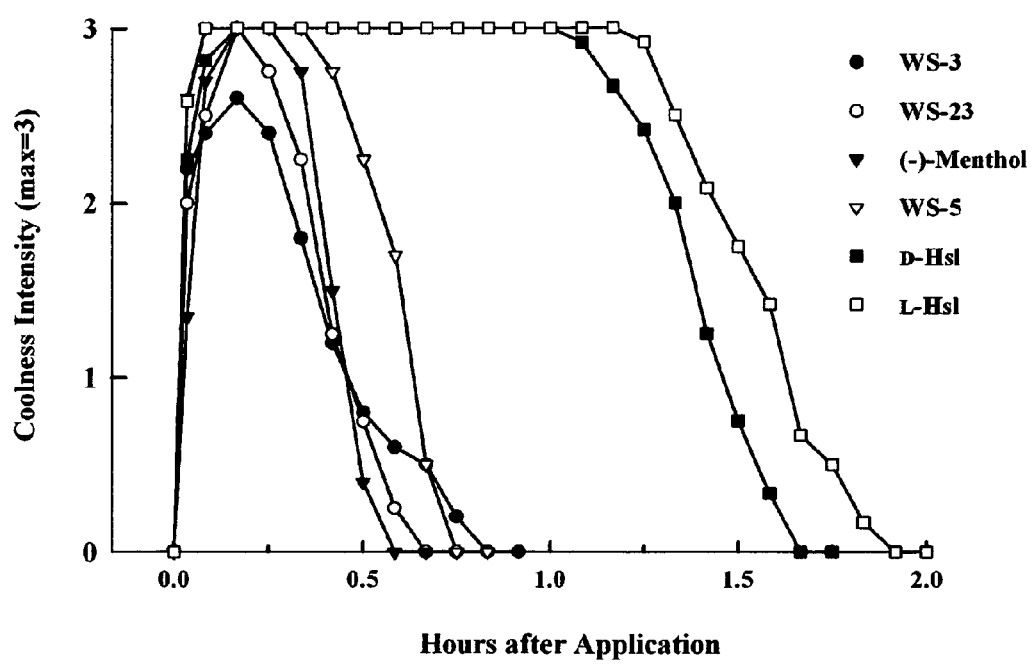

N ALKYLCARBONYL AMINO LACTONE COMPOUNDS AND THEIR USE

This application is a continuation-in-part of U.S. patent application Ser. No. 11/910,185, filed Sep. 28, 2007, now abandoned, inventor Wei, entitled "N-Alkylcarbonyl-Amino Acid Ester and N-Alkylcarbonyl-Amino Lactone Compounds and Their Use", incorporated by reference.

RELATED APPLICATIONS

This application is related to:
U.S. Provisional Application No. 60/667,166 filed 29 Mar. 2005;
U.S. Provisional Application No. 60/683,384 filed 20 May 2005;
U.S. Provisional Application No. 60/702,505 filed 26 Jul. 2005;
U.S. patent application Ser. No. 11/203,728 filed 13 Aug. 2005; and
U.S. Provisional Application No. 60/772,374 filed 9 Feb. 2006;
the contents of each of which are incorporated herein by reference in their entirety.

TECHNICAL FIELD

The present invention generally relates to refreshing, soothing, and cooling compounds that affect sensory processes. More particularly, the present invention pertains to certain N-alkylcarbonyl-amino lactone compounds; compositions and articles comprising such compounds; and methods of treatment, for example, methods of alleviating the discomforts of irritation, itch, and pain in the skin and in the linings of the oral cavity and upper respiratory tract, for example, in methods of treatment of cough and/or asthma.

BACKGROUND

Menthol and menthol-like compounds are used in toiletries, confectionery, comestibles, and over-the-counter medications as ingredients to refresh, cool, flavor, counter-irritate, and anesthetize the skin and mucous membranes of the mouth and upper airways. Menthol's utility in relief of sensory discomfort is, however, limited by its short duration of action and by its multimodal actions on sensory processes—including odor, harshness of taste, and irritation.

Current treatments for the discomforts of injured skin include cold water rinses or compresses, and ointments containing local anesthetics (such as EMLA®), non-steroidal anti-inflammatory analgesics (NSAIDs), or anti-inflammatory steroids (e.g. 1% hydrocortisone cream). Current medications for cough are dextromethorphan, codeine, and menthol. These methods and compounds have moderate effectiveness and ease of use. There is a need for compounds like menthol that refresh, cool, and soothe the body's surfaces, but without the disadvantages of odor, irritancy, and a short duration of action. In order to treat medical discomforts of the skin, such as pruritic eczema, or sustained coughing, it is important to have compounds that act longer than menthol.

About three decades ago, a group of scientists synthesized over 1200 compounds in an attempt to find cooling agents that had properties better than menthol. Their results were summarized in a paper (Watson et al., "New compounds with the menthol cooling effect," J. Soc. Cosmet. Chem., 29: 185-200, 1978). From this research, an N-alkyl-cycloalkyl- and an N-alkyl-alkyl carboxamide, WS-3 and WS-23, were brought to the market and are used as additives for confectionery, comestibles, (e.g., candy, chewing gum), and toiletries.

In U.S. Pat. No. 4,178,459 (11 Dec. 1979), Watson et al. described cooling properties of some N-alkoxycarbonylalkyl-substituted p-menthane-carboxamides. The recent information on cooling agents used for topical applications was reviewed by M. B. Erman ("Cooling agents and skin care applications," Cosmetics & Toiletries, 120: 105-118, May 2005; "Progress in physiological cooling agents," Perfumer & Flavorist, 29: 34-50, 2004) and by P. Jacobs and W. Johncock ("Some like it cool," Parfumerie and Kosmetik, 80: 26-31, 1999).

None of the compounds currently known to the art have the potency or duration of action to qualify them as possible prescription medications for use in skin disorders such as pruritic eczema or in upper respiratory ailments such as cough.

SUMMARY OF THE INVENTION

One aspect of the present invention pertains to certain N-alkylcarbonyl-amino lactone compounds, as described herein.

Another aspect of the invention pertains to a composition comprising such a compound and a delivery vehicle (e.g., for delivering the compound to a human).

In one embodiment, the delivery vehicle is a pharmaceutically acceptable carrier or diluent.

In one embodiment, the delivery vehicle is adapted to deliver the compound to the skin of the human.

In one embodiment, the delivery vehicle is a towelette.

In one embodiment, the delivery vehicle is adapted to deliver the compound to the oral cavity and/or the upper respiratory tract of the human.

In one embodiment, the compound is present in the composition in an amount of 1 to 10 mg, for example, in an orally disintegrating tablet (ODD.

In one embodiment, the compound is present in the composition in an amount of 0.1 to 5% wt/vol.

In one embodiment, the composition further comprises a polyhydric alcohol.

In one embodiment, the composition further comprises a mucoadhesive polymer.

Another aspect of the present invention pertains to methods of treatment of the skin, oral cavity, or upper airways of a human, comprising: contacting a composition comprising such a compound and a delivery vehicle with the skin, oral cavity, or upper airways of the human, thereby delivering an effective amount of the compound to the skin or mucous membranes of the human.

Another aspect of the present invention pertains to such a compound for use in a method of treatment of the human or animal body by therapy.

Another aspect of the present invention pertains to use of such a compound in the manufacture of a medicament for use in a method of treatment.

In one embodiment, the treatment alleviation of skin irritation, itch, and/or pain (e.g., wherein the contacting delivers an amount of the compound that is therapeutically effective for alleviation of skin irritation, itch, and/or pain).

In one embodiment, the treatment is alleviation of cough and/or the sense of irritation and/or obstruction of the upper airways (e.g., wherein the contacting delivers an amount of the compound that is therapeutically effective for alleviation of cough and/or the sense of irritation and/or obstruction of the upper airways).

In one embodiment, the treatment is of cough (e.g., wherein the contacting delivers an amount of the compound that is therapeutically effective for reducing the frequency of cough).

In one embodiment, the treatment is treatment to increase alertness, or to decrease nausea, appetite, or fatigue (e.g., wherein the contacting delivers an amount of the compound that is effective to increase alertness.

As will be appreciated by one of skill in the art, features and preferred embodiments of one aspect of the invention will also pertain to other aspect of the invention.

Other advantages and aspects of the invention will be understood by reading the following detailed description and the accompanying claims.

BRIEF DESCRIPTION OF THE DRAWINGS

FIG. 1 is a graph showing duration of cooling (hours) for six compounds (in order, left to right): WS-3, WS-23, (−)-menthol, WS-5, D-Hsl (no. 1 in Table A), and L-Hsl (no. 2 in Table A). The durations of cooling effects of known agents, e.g., (−)-menthol, WS-3, WS-23 and WS-5 are ≦0.5 hr, and relatively short compared to the D-Hsl and L-Hsl lactone compounds of >1 hr. The presence the lactone ring in D-Hsl increases duration of action and these compounds are examples of the preferred embodiments of this invention.

DETAILED DESCRIPTION

A class of compounds that is suitable to be used as an active ingredient in (e.g., pharmaceutical) preparations for use on skin, lips, and mucous membranes of the oral cavity and upper respiratory tract has been found.

These compounds are suitable, for example, for use as therapeutic agents, to reduce discomfort such as itch and pain, and as additives for comestibles, confectionery, cosmetics, and toiletries.

These compounds have one or more of the following properties:
  a refreshing, soothing, and cooling action on surfaces of the skin, oral cavity, and/or throat, and, in pathological states, exert an anti-irritant, anti-pruritic, antitussive, and/or anti-nociceptive effect;
  a minimal irritant action on the eye when the compound is applied to the ocular surface or the facial skin near and around the eyes, for example, when applied to the malar and periorbital skin (indicating also a good safety profile), for example, when applied on the ocular surface at a concentration of 1 mg/ml (0.1% wt/vol) or on the skin at a concentration of ~5 to 10 mg/ml, equivalent to a 0.5 to 1% wt/vol mixture;
  a rapid onset of action of less than about 3 to 5 minutes, for example, when applied on the skin at a concentration of 10 mg/ml or less, equivalent to a 1% wt/vol mixture;
  a duration of action that exceeds 1 hour, for example, when applied on the skin at a concentration of 10 mg/ml or less, equivalent to a 1% wt/vol mixture;
  wherein repeat applications do not result in altered sensitivity to subsequent stimulation; and
  a potent cool, soothing, and refreshing sensation when applied into the oral cavity that counteracts irritative stimuli in the mouth and upper airways that causes cough and wheezing.

These compounds may conveniently be referred to as N-alkylcarbonyl-D-, L-, or DL-amino lactones, or "NACL compounds".

In preferred embodiments, the compound is selected from compounds of Formula (I):

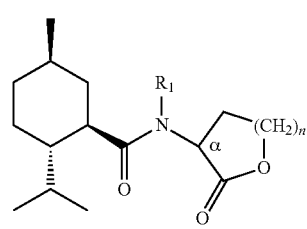

Formula (1)

wherein:
n is independently 1, 2, or 3; and
$R_1$ is independently hydrogen or methyl.

For compounds of Formula (1), the α-carbon may independently be in the D-amino acid configuration (i.e., (R)-configuration) or the L-amino acid configuration (i.e., (S)-configuration. Both enantiomers, and (e.g., racemic) mixtures thereof, are approximately equipotent in biological terms. The chiral center of the lactone is such that there may be no significant energy barriers in assuming either of the active configurations. Thus, a racemic mixture of the lactone may also be useful.

Homoserine (Hse) may be cyclized to form a five-member lactone ring (a γ-lactone ring) referred to as homoserine lactone (Hsl). Consequently, compounds of Formula (1), wherein n is 1, and $R_1$ is independently hydrogen are referred to herein as D-Hsl, L-Hsl, and D/L-Hsl analogs (or as No. 1, 2, or 3 in Table A).

Examples of some preferred compounds include the following:

TABLE A

Preferred Compounds

| | | | |
|---|---|---|---|
| 1 | D-Hsl | (1R,2S,5R)-2-isopropyl-5-methyl-cyclohexane-carboxylic acid ((R)-2-oxo-tetrahydro-furan-3-yl)-amide | |
| 2 | L-Hsl | (1R,2S,5R)-2-isopropyl-5-methyl-cyclohexane-carboxylic acid ((S)-2-oxo-tetrahydro-furan-3-yl)-amide | |
| 3 | D/L-Hsl | racemic (1R,2S,5R)-2-isopropyl-5-methyl-cyclohexane-carboxylic acid ((R/S)2-oxo-tetrahydro-furan-3-yl)-amide | |

Additional examples of preferred compounds include the following:

| | |
|---|---|
| a. | (1R,2S,5R)-2-isopropyl-5-methyl-cyclohexanecarboxylic acid methyl-((S)-2-oxo-tetrahydro-pyran-3-yl)-amide |
| b. | (1R,2S,5R)-2-isopropyl-5-methyl-cyclohexanecarboxylic acid methyl-((R)-2-oxo-tetrahydro-pyran-3-yl)-amide |
| c. | (1R,2S,5R)-2-isopropyl-5-methyl-cyclohexanecarboxylic acid methyl-((R/S)2-oxo-tetrahydro-pyran-3-yl)-amide |

Additional examples of preferred compounds include the following:

| | |
|---|---|
| a. | (1R,2S,5R)-2-isopropyl-5-methyl-cyclohexanecarboxylic acid ((S)-2-oxo-tetrahydro-pyran-3-yl)-amide |
| b. | (1R,2S,5R)-2-isopropyl-5-methyl-cyclohexanecarboxylic acid ((R)-2-oxo-tetrahydro-pyran-3-yl)-amide |
| c. | (1R,2S,5R)-2-isopropyl-5-methyl-cyclohexanecarboxylic acid ((R/S)2-oxo-tetrahydro-pyran-3-yl)-amide |
| d. | (1R,2S,5R)-2-isopropyl-5-methyl-cyclohexanecarboxylic acid methyl-((S)-2-oxo-tetrahydro-pyran-3-yl)-amide |
| e. | (1R,2S,5R)-2-isopropyl-5-methyl-cyclohexanecarboxylic acid methyl-((R)-2-oxo-tetrahydro-pyran-3-yl)-amide |
| f. | (1R,2S,5R)-2-isopropyl-5-methyl-cyclohexanecarboxylic acid methyl-((R/S)2-oxo-tetrahydro-pyran-3-yl)-amide |

Additional examples of preferred compounds include the following:

| | |
|---|---|
| a. | (1R,2S,5R)-2-isopropyl-5-methyl-cyclohexanecarboxylic acid ((S)-2-oxo-tetrahydro-oxepan-3-yl)-amide |
| b. | (1R,2S,5R)-2-isopropyl-5-methyl-cyclohexanecarboxylic acid ((R)-2-oxo-tetrahydro-oxepan-3-yl)-amide |
| c. | (1R,2S,5R)-2-isopropyl-5-methyl-cyclohexanecarboxylic acid ((R/S)2-oxo-tetrahydro-oxepan-3-yl)-amide |
| d. | (1R,2S,5R)-2-isopropyl-5-methyl-cyclohexanecarboxylic acid methyl-((S)-2-oxo-tetrahydro-oxepan-3-yl)-amide |
| e. | (1R,2S,5R)-2-isopropyl-5-methyl-cyclohexanecarboxylic acid methyl-((R)-2-oxo-tetrahydro-oxepan-3-yl)-amide |
| f. | (1R,2S,5R)-2-isopropyl-5-methyl-cyclohexanecarboxylic acid methyl-((R/S)2-oxo-tetrahydro-oxepan-3-yl)-amide |

Preferred among these long-acting NACL compounds are those when applied to the skin or mucous membranes, produce refreshing, soothing, and cooling sensations without skin irritation, with minimal eye irritation, and with a duration of action on skin that lasts more than about 1 hour when used at 10 mg/ml or less, and a duration of action on the linings of the oral cavity and upper respiratory tract that last for more than about 30 minutes.

The traditional cooling N-alkyl substituted carboxamides described by Watson et al. [e.g., WS-3, WS-5, WS-12, and WS-31], have short durations of action of 18, 33, 25 and 20 min, respectively, when tested at ~10 mg/ml on the skin (see Tables 4 and 5) These molecules have a relatively slow onset of action ($\geqq$4 min) and are suitable only for use in comestibles, confectionery, and toiletries. Watson et al. did not consider lactone ring compounds. The long-acting NACL compounds, as shown in FIG. 1 and Tables and 3, have a fast onset of ~2 min and act for over an hour.

Some of the tested WS compounds did not achieve significant cooling but rather produce skin sensations of tingling, burning, and irritation, effects that are similar to those observed with menthol, a compound with multimodal actions of sensory processes. By contrast, the preferred NACL compounds deliver a perfect cooling sensation and minimal skin or eye irritation. Thus, cyclization of the α-carbon of the amino acid to the alkyl moiety of the ester in order to form, for example, a 5-membered γ-lactone ring resulted in compounds with the desired bioactivity. These NACL also have long duration of action when applied to the ocular surface and inhibit the sensory stimuli elicited by chili pepper sauce in the pharynx (a model of antitussive activity).

Due to their prolonged activity, the NACL compounds, compositions, and articles may be used therapeutically, for example, to reduce discomforts associated with pathophysiological manifestations of injury and inflammation on cutaneous and upper alimentary and respiratory surfaces of the body.

These compounds may be used on skin and in the oral cavity/pharynx to counteract irritation, itch and pain in therapeutic situations where prolonged relief of sensory discomfort is desired such as for intense pruritic eczema and for coughing.

These compounds inhibit the perception of itch, pain, and discomfort from the skin and the mucous membranes of the oral cavity and upper respiratory tract, and so can be used in the inhibition of sensory disorders in these tissues.

These compounds (for example, when formulated in an ODT or a liquid at unit doses of up to 50 mg) have rapid onset of less than 1 minute, soothe the throat, and have potent antitussive action exceeding several hours, with no irritation to the mouth or airways. These compounds are without odor, smarting, or burning sensations on the facial skin or in the mouth.

The compounds are useful by themselves and/or in compositions further comprising a delivery vehicle, such as a delivery vehicle for delivering the compound to skin. In one embodiment, the compound is carried on a towelette adapted for, or of sufficient construction for, the delivery of a dermatologically effective amount of the compound to the skin.

The prolonged duration of action permits use of NACL embodiments in therapeutic situations where discomfort of skin or mucous membranes is present for at least one day, for example, in allergic dermatoses, dermatitis of the facial skin, or after severe insect bites.

Currently, there are no topical cooling analgesic medications approved in this category for therapeutic relief of skin discomfort, although the demand exists for such substances. The potent Hs1 derivatives, among others, with selective cooling and refreshing actions, also increase the scope of agents that may be used in the oral cavity and upper respiratory tract and may be incorporated into therapeutics such as antitussive formulations.

The specific structural features of the molecules that confer the desired properties of increased potency, namely the presence of the lactone ring and of refreshing cooling without irritation, were unexpected and surprising and not known in the prior art.

Pharmacology and Mechanisms of Action of N-Alkylcarbonyl-Amino Lactones (NACL)

Noxious stimuli from the skin and mucous membranes are thought to be transmitted by unmyelinated C fibers and thinly myelinated Aδ fibers. There are many conditions that produce sensory discomforts on the skin and in the mucous membranes of the mouth and upper airways, discomforts which are ameliorated by cooling. Cooling of the facial skin and mucous membranes is detected by a subset of primary sensory afferents that have receptors on nerve endings. These sensory fibers exhibit a rhythmic, ongoing discharge at neutral temperatures that increases in response to skin temperature cooling (step reductions from 33 to 23° C.) and are suppressed by warming. The dynamic information is propagated along axons in spike trains, at about 20 to 40 impulses/sec, to central neurons, leading in humans to cooling sensations. This type of sensation is mimicked by facial exposure to air or water temperatures of 15 to 22° C. The primary afferents from facial skin terminate in the superficial layer of the caudal trigeminal nucleus where they represent over 95% of the thermoceptive input (see, e.g., Hutchinson et al., J. Neurophysiol., 77:3252-3266, 1997). The cooling signals from the nasopharynx and the oropharynx are transmitted via the glossopharyngeal nerve.

Temperature detection inputs from the face and lips are especially important for modulating behavior as this surface is densely innervated, as can be seen in diagrams of the sensory homunculus in textbooks of psychology. This fact is readily experienced as we notice temperature changes easily from sensations on our face and ocular surface but less so from other parts of our body. Thermosensation from the face is dominated by these cold receptor signals which are tonically active.

Coolness signals detected from the oral cavity are more complex, because the precise identification of the signal may be confounded by variables such as the secretion of saliva and gustatory signals mediated by the facial and glossopharyngeal nerves that are distinct from the trigeminal input.

The precise mechanisms underlying the benefits of refreshing cooling on sensory discomfort are not clearly understood, although such benefits are a common experience. In order to treat skin discomfort, a compound must act for at least one hour and preferably longer, otherwise the patient would have to repeatedly apply the drug to obtain relief. For an anti-irritant or antitussive action in the airways, the ideal agent should have rapid onset of action, soothing effects, and the ability to relieve discomfort for an extended duration, for example, for several hours.

Non-Technical Description of Inventive Concept

Using recording electrodes, cool and hot signals entering the brain (see Hutchinson et al., vide supra) were converted to audio signals. The "cool" neurons generate a "pitter-patter" sound, like raindrops falling on a rooftop. These neurons are tonically active at room temperature. Further cooling, for example, with an ice-cube brought near the receptive surface, increases the sound and frequency of the "pit-pat" to that of a strong shower. By contrast, the "heat/pain" neurons are silent until a heat source brings the skin temperature near 43.3° C. Then these neurons discharge in synchrony with a roar, like the sound of high surf or tide coming onto a beach. The pit-pat and roar of cool and hot neurons are modality specific and not activated by pressure or touch. It is believed that the NACL compounds described herein set the pitter-patter transmission of cool neurons so that the brain perceives the ambient temperature at about 15 to 18° C. Activation of these neurons is like turning on a robust air-conditioner within a hot environment. This sensory band in normal individuals is felt as alerting, refreshing, and cool. This is referred to herein as the "perfect cool." The presence of the NACL compounds and the perfect cool, in pathological conditions, gates the passage of noxious heat-like signals into the spinal cord and/or brain. Hence, a soothing anti-nociceptive (anti-irritant, anti-pruritic and antitussive) effect is achieved with therapeutic benefit.

The inventor has identified NACL molecules with potent and prolonged activation of the perfect cool. These molecules are qualitatively and quantitatively unlike (−)-menthol and WS-3 which act for less than 20 minutes. In certain cases of itch and cough, it was also observed that the NACL compounds exerts prolonged anti-nociceptive activity when the sensations of the perfect cool no longer reach conscious perception, and that repeated applications of the NACL compounds can silence and extinguish nociception. These results suggest that the perfect cool may further modulate and attenuate the plasticity of the nociceptive process.

The NACL compounds are active at single doses of 1 to 10 mg and at concentrations of 10 mg/mL or less when applied topically to the surfaces of the body. By topical, it is meant that the application is onto surfaces of the body in contact with air, which includes the facial skin, the eyelids, the lips, the upper respiratory tract, and the entrance and exit of the gastrointestinal tract, namely, the oral cavity and the anorectum.

The NACL compounds also have a rapid onset of action (from about 0.5 to about 3 minutes) relative to other compounds (see, e.g., FIG. 1 and Studies). The onset and offset of action of these compounds was first revealed by testing on the facial skin of subjects and then subsequently by applying them to the ocular surface and to the oral cavity/oropharynx.

Bioassays of N-Alkykarbonyl-Amino-Lactones

Psychic events such as refreshment, soothing, cooling, irritation, itch, and pain cannot be verbalized by animals (animals cannot say "it feels cold", "ouch", or that "it itches"). Hence, the sensory effects of chemicals in animals must be indirectly inferred. Receptor assays, based on cells transfected with the genes for proteins associated with thermosensation (e.g., TRP-M8, TRP-A1, TRP-V1) may be used as a model of sensory processes. The receptor assays yield quantitative data. However, these assays give no information on onset and offset of action, or on the quality of human sensations evoked by the chemicals. Thus, the best information on the pharmacological properties of chemicals is derived from direct tests on humans.

Watson et al. (U.S. Pat. No. 4,178,459) tested the properties of N-substituted p-menthane carboxamides on volunteers by putting filter paper (1×1 cm), impregnated with a known amount of compound, onto the dorsal surface of the tongue of the test subject. After 30 seconds, the subject was required to report presence or absence of a cooling effect. These data were reported as "Threshold, µg" and refer to the threshold amount of the test substance that produces cooling sensations upon application onto the tongue of a panel of human volunteers. The average threshold of (−)-menthol for 6 subjects was 0.25 µg, but there was a 100-fold variation in individual sensitivity. As noted above, coolness signals detected from the dorsal surface of the tongue may be confounded by gustatory, olfactory, and other variables, as well as by dilution from saliva.

It has been found that, if the goal is to find a drug useful for topical application, the refreshing cooling and sensory properties of a NACL compound are best tested first by suspending or dissolving a test substance in an ointment (usually Aquaphor®, which is 41% petrolatum, and the rest mineral oil, ceresin and lanolin alcohol) and singly applying the ointment (40 to 70 mg) onto the skin surface using a plastic stick. A reliable place for topical application is the skin above the upper lip (above the vermilion border of the lips), on the philtrum, lateral to the philtrum until the nasolabial folds, and on the lower nostrils (subnasale). This part of the face is known to be densely innervated with cold receptors, second only to the surfaces of the eyeball and anogenitalia. At this site, tingling, cool and cold sensations in the skin may be experienced and rated for time of onset and intensity.

The intensity of the subjective skin sensation is rated as 0, 1, 2 or 3 with: 0 as no change; 1 as slight coolness, cold, or tingling; 2 as clear-cut signal of coolness, cold, or tingling; and 3 as robust cooling or cold. The intervals for recording sensations are 5 to 10 minutes, until two successive zeroes are obtained. The results (shown in FIG. 1) are averaged values of 4 to 6 separate trials in the same individual. The data are plotted using SigmaPlot® (Systat Software, Point Richmond Calif.) and a smoothing function with a negative exponential was used for analysis and statistical fit of the results. Confirmatory trials of cooling action of the NACL compounds were obtained in 2 to 4 individuals.

The onset of drug action is taken as the time to reach 2 units of coolness intensity, and offset of drug action is the time when coolness intensity drops below 2, after previously surpassing 2 units. The duration of cooling action is defined as the offset time minus the onset time. An inactive compound is defined as one that does not exceed 2 units of cooling for 5 minutes after application. The quality of the sensation is noted, for example, as pure refreshing coolness, or if the sensation is accompanied by irritation (stinging or burning). The quality of the sensation is not rated for intensity.

The ointment is also applied to the periorbital skin (upper and lower eyelids and on skin adjacent to the lateral canthus) for tests of irritancy near the eyes, and the subject is asked if irritation is present or absent. The intensity of the eye sensation is not rated. The sensory information described above is not obtainable in a receptor assay. For a topical agent, the most reliable results are therefore first derived from direct tests on the skin. The next target for testing is the receptors in the oral cavity and the upper airways. Taste thresholds are difficult to quantify on the tongue because of the dynamic fluid conditions in the oral cavity and the presence of taste and adaptive factors that affect thermosensation on the tongue. The oral cavity tolerates extremes of hot and cold temperatures that are not acceptable on the skin. For example, hot beverages (such as coffee) are tolerated at temperatures in the mouth that are considered painful and scalding when spilled on the skin. Also, ice-cold drinks may be refreshing in the mouth, but an ice-cube on the skin quickly becomes unpleasant.

It has been found that an effective method for testing a compound for effects in the oral cavity is to take a 1 to 5 mg sample and place it on the dorsal surface of the tongue, ⅔ posterior from the tip and in the midline. The subject is instructed to close and hold the substance in the mouth for at least 10 seconds and not to swallow. The description of sensations is then recorded at 5 minute intervals.

The method for the evaluation of compounds in the oral cavity was further refined for tests for upper pharyngeal irritation, the goal being to find an effective ingredient in the treatment of cough. This chili pepper sauce method is described in Study 1.

Qualitative Aspects of Cool and Cold Intensity

The static and dynamic temperatures of the skin give rise to sensations that are qualitatively distinct. The normal skin temperature is 32 to 34° C. and when water is applied to the skin, it is called: tepid at 27 to 32° C.; cool between 18 to 27° C., cold at 13 to 18° C., and very cold below 13° C. A critical range of room temperatures for coolness and cold is at 18 to 22° C. For example, a sedentary individual, dressed lightly, will frequently want to turn up the thermostat when the room temperature drops one or two degrees below 20° C. (68° F.). In gaming establishments, air temperatures are deliberately kept at 18 to 20° C. in order to arouse, increase vigilance, and activate gambling activities. In the outdoors, breathing cool air at 15 to 21° C. is refreshing, invigorating, and alerting, and the emotional response may be positive and joyful. At ambient or surface skin temperatures of 15° C. (55° F.) or below, however, the cold sensation become painful and aversive and is accompanied by affect; that is, the person considers these cold sensations to be unpleasant, seeks to escape the environment, and may become angry, hostile, or irritable if escape is not possible.

The NACL compounds described herein are useful as a topical agent for the relief of skin discomfort, and mimic the effects of running cold water on injured skin. The "nominal" ambient skin surface temperature to mimic with a cooling agent is in the range of 15 to 22° C. The effect can also be simulated by putting a towel wet with water at room temperature onto the face. The coolness of a wet towel will rapidly dissipate, an effect called adaptation, even when the cooling stimulus is still there. On the other hand, for a chemical agent applied to the facial skin, the stimulus is more constantly present. The exact physiological sensation to replicate with the inventive compounds is that of refreshing, soothing coolness, with minimal or no sensations of irritation or sting, and the absence of excessive cold.

As shown in the Studies, the preferred NACL compounds, tested at ~10 mg/ml, produce cooling sensations on the facial skin, have a rapid onset of action (less than 5 minutes) and slow offset (more than 1 hour). By contrast, various structurally similar compounds were either inactive or had a short duration of action, as shown by comparative data in FIG. 1 and in the Studies.

The long duration of action of some preferred NACL compounds, e.g. the Hs1 analog, was unexpected and surprising. On the tongue of normal subjects, the effects of a NACL compound may elicit an initial "tickle" of 1 to 3 seconds, then the onset of robust and refreshing cooling could be detected. Usually, at a dose of 2 to 4 mg of a NACL compound, the cooling sensations lasted for about 30 minutes. Surprisingly, in subjects with cough or irritative stimuli originating from the throat, there was rapid (within 1 minute) attenuation of sensory discomfort and the cessation of coughing. Also surprisingly and unexpectedly, the duration of the antitussive effect lasted for at least several hours and occurred when the cooling sensations were no longer detected. This soothing effect on the oropharynx and throat was especially beneficial to subjects who had frequent cough.

Use of N-Alkylcarbonyl-Amino Lactones on the Face and Other Surfaces

In a preferred use, the NACL compounds is topically applied to therapeutically relieve the irritation, itch, and/or pain of inflamed skin and/or of inflamed tissues in the oral cavity and/or upper respiratory tract.

Other contemplated uses include long-term refreshment of the facial skin and to increase alertness and vigilance.

Contemplated non-therapeutic uses include use as ingredients in comestibles (e.g. chewing gum, mouth-washes, anti-gingivitis products, toothpastes), cosmetics, lipsticks, flavors, tobacco additives, confectionery, or toiletries.

By "topically" it is meant application onto surfaces of the body in contact with air, which includes the skin, the eye surface, the lips, the upper (nose) and lower respiratory tracts, and the entrance and exit of the gastrointestinal tract, that is, the oral cavity and the anorectum. Particularly favored sites of application are the surface tissues of the face and head innervated by the trigeminal nerve which includes the skin, scalp and the linings of the orbit, lips, nose and mouth. A second favored site is the nerve endings of the glossopharyngeal nerve in the naso- and oro-pharynx.

By "oral administration" it is meant delivery of the active ingredient as solid, liquid, or aerosol, into the oral cavity, preferably in a delivery vehicle.

For topical uses, a NACL compound is preferably formulated so as to have fast onset and slow offset.

Preferably, the compound does not sting or irritate when applied on the face near the orbit, and produces more refreshing cool than cold.

Some of the uses may be further categorized as:

Therapeutic: A NACL compound may, for example, be used as a local analgesic on inflamed skin or as an anti-pruritic. It may also be orally administered as an antitussive or anti-irritant in the oral cavity.

Anti-irritant: A NACL compound may be incorporated into a skin care product that contains irritating substances, such as retinoids or $\alpha$-, or $\omega$-fatty acids.

Arousal: In normal, healthy individuals, the NACL compounds may be used to alert and to refresh, to counteract fatigue, and to relieve the individual from heat exhaustion, nasal and eye irritation, and obstructed breathing discomfort. It may be used to enhance a bright-eyed and alert look because of its refreshing properties. It may be valuable for athletes training in a hot environment, for example, baseball players in Arizona during spring training or soccer players in Spain or South America.

Cleansing: A NACL may be incorporated into a towelette for removing make-up, especially for mascara around the eyes.

Food and personal care products: A NACL compound may be incorporated into comestibles (e.g., chewing gum, toothpastes), cosmetics, lipsticks, flavors, confectionery, tobacco, beverages, or toiletries, to provide sensory refreshment.

Therapeutic uses for topical formulations of one or more NACL compounds are contemplated in a towelette, lotion, cream, ointment, or in oral or inhaled formulations, and include utility for:

alleviation of irritation, itch, and/or pain from various forms of dermatitis (atopic, contact, and irritant), pain from burned, traumatized, or irritated skin (e.g., facial surgery), and from procedures related to wound debridement, itch and discomfort from skin infections, insect bites, sunburn, photodynamic treatment of skin (e.g., actinic keratoses, basal cell carcinoma), pruritus due to xerosis, mucositis and stomatitis from, for example, apthous ulcers or cancer chemotherapy, cheilitis or itching of the lips from cold sores and gingivitis, pruritus ani, hemorrhoidal discomfort, pain from anal fissures, pain or itch from anal fistulas, pain from hemorrhoidectomy, perineal inflammation, anogenital skin inflammation, and discomfort due to various local causes such as incontinence, diaper rashes, perineal inflammation, upper airway discomfort from breathing obstruction, e.g., cough, rhinitis, bronchitis, and chronic obstructive pulmonary diseases, dyspnea, and sleep apnea, and conjunctivitis, ocular surface irritation, pain from corneal abrasions, and pain from eye surgery.

Pharmacology of N-Alkylcarbonyl-Amino Lactones in Counter-Acting Cough

Coughing is a familiar human experience and is executed by a coordinated contraction of the respiratory muscles against a closed glottis. The sudden opening of the glottis results in an explosive outburst of air and this flow is designed to remove sensory irritants and obstructions from the airways.

Thus, cough is a protective reflex. The sensations that lead to cough are multi-factorial and include conditions such as airway infections, allergies, inflammation of the airways from pollutants, pharyngitis, laryngitis, and from chronic conditions such as asthma, chronic obstructive lung disease, gastroesophageal reflux disease, lung cancer, pneumonia, pulmonary edema, and congestive heart failure. The "urge to cough" can be modulated by the brain, so, for example, individuals can suppress cough during a concert or opera. Alternatively, during the night when sensory inputs to the brain are diminished, the stimulus for cough is now amplified and the individual coughs more as a result.

The throat is a loose anatomical term describing the region of the body around the voicebox. Internally, an important structure for cough is the lower pharynx. The pharynx is divided into three regions: naso, oro and laryngo. The oropharynx is especially a busy traffic zone as everyday for the adult an average 12,000 L of air and 2 kg of food pass through, and it is essential for survival that the traffic flow is correct and food does not go into the airways. The swallow reflex and the cough reflex protect the airways against solid particles. The narrowest point of the traffic zone is called the lower retropalatal oropharynx (LRO) and has a cross-section of about 1 cm$^2$.

I believe that a NACL of this discovery delivered to the LRO via a rapid orally disintegrating tablet (ODD is an effective drug method for the treatment of cough.

The neurophysiological mechanisms of drug action is based on cooling signals that indirectly "gate" the perception of noxious stimuli that produce the sensations for and the urge to cough. The afferent cooling signal from the oropharynx is via the 9th cranial nerve (glossopharyngeal nerve) and the cough signals, thought to originate from the pharyngeal, laryngeal, oesophageal, and bronchial epithelium, may be carried by the 5th, 9th, and 10th cranial nerves. For the ODT cough tablet, it is believed that the mechanism of action is for the cooling signals from the nerve endings of the orpharynx to enter into the brainstem via the 9th nerve and then "gate" the irritant cough signals coming into the brainstem from the other cranial nerves.

I believe the concept of a ODT, containing a robust cooling agent delivered to the LRO for the pharmacological management of cough, is new and has not been previously described. The three drugs commonly used for treating coughing are dextromethorphan, codeine, and menthol. In addition, sedative antihistamines, local anesthetics, mucolytics, benzonate, and sugar solutions such as honey are also used. All of these methods in practice do not have ideal properties because they either have side-effects or do not work well when the coughing is severe. No new medications for cough have been introduced in the past fifty years. Current medications for coughing have limited efficacy, as witnessed by individuals who stay awake at night, unable to sleep because of cough, and individuals who cough for prolonged periods, for example, for 3 weeks after a viral infection of the upper airways. There is need for a new medication, simply applied, that is not invasive on brain chemistry and which will control cough for at least three to four hours to allow the individual to stop coughing and go to sleep.

The formulations of a ODT for drug delivery are known to those skilled in the art (for example, (see Reddy et al. Rapidly disintegrating oramucosal drug delivery technologies. Pharmaceutical Development and Technology 14: 588-601, 2009). Rapid orally disintegrating tablets are defined by the Food and Drug Administration (U.S.) as "A solid dosage form containing medicinal substances, which disintegrates rapidly, usually within a matter of seconds, when placed upon the tongue." Further refinement of this definition states that the tablet dissolves in the saliva and disintegrates in vitro or in vivo in 30 sec or less, and "The products are designed to disintegrate or dissolve rapidly on contact with saliva, thus eliminating the need for chewing the tablet, swallowing an intact tablet, or taking the tablet with water (Guidance for Industry: Orally Disintegrating Tablets. FDA-Center for Drug Evaluation and Research, April 2007)." Examples of such ODT formulations are sold as OTC products, for example, Sedalia® (for stress) and Sabadil® (for allergy) by Boiron®. Here the excipients are lactose, croscarmellose sodium (carboxymethylcellulose), and magnesium stearate and individual tablets are stored in blister packs and each weigh 240 to 260 mg. These tablets dissolve in saliva within 15 sec after placement on the dorsal surface of the tongue. As contemplated here, however, smaller ODT weighing 60 to 100 mg are sufficient to achieve control of excessive cough.

The ODT, as known to the art, is designed for rapid delivery of an active ingredient into the bloodstream and hence to deliver the drug to target receptors distant from the site of application (e.g. as in anti-migraine and anti-psychotic drugs). As contemplated here, however, the ODT is a specialized means for localized topical delivery to the pharyngeal epithelium of the LRO. This particular method of drug delivery for the treatment of cough has not, to my knowledge, been previously described. ODT for drug delivery to the buccal mucosa are known to the art.

The formulated ODT tablet described and tested here weigh 60 to 100 mg and dissolves in saliva within 15 seconds after application to the dorsal surface of the tongue. The onset of cooling action occurs in about 0.5 to 3 minutes. The duration of cooling sensation is about 15 to 30 minutes, but the anti-cough actions last for several hours.

Limitations of Menthol Lozenges in the Treatment of Cough

The public is familiar with menthol cough drops (also called lozenges or troches). No placebo-controlled studies have been published to demonstrate the effectiveness of menthol lozenges in the treatment of cough.

The neuropyschological mechanisms underlying the refreshing cooling of (−)-menthol are not understood. Sensations can be "confusing" when a chemical affects more than one sensory modality. This is especially true for (−)-menthol (also known as l-menthol, (1R)-menthol, and (1R,2S,5R)-menthol). Menthol is widely used as a cooling agent but it has multimodal action on sensory processes. For example, in the upper airways and oral cavity, menthol can elicit somatosensation (cooling, irritation, tingling), olfaction (minty), and gustation (bitter). As a counter-irritant, menthol can briefly reduce irritation of oral and pharyngeal membranes (e.g., strong mints or toothpastes) and have analgesic actions on muscle (e.g., BenGay® ointment). The multimodal actions of menthol may further mix to give rise to complex perceptions of irritation (burning, prickling, stinging), especially around the eyes, of thermal effects (cooling, warming) and of tactile effects (buzzing, tingling, tickling, numbing). In the nose and oral cavity, the predominant mode of detecting menthol is olfactory (see, e.g., Nagata et al., J. Exptl. Psychol., 31: 101-109, 2005). The strong cooling sensations of mint candies such as Mentos in the nasal cavity come from retronasal delivery of volatilized menthol in the breath onto nasal membrane receptors.

A lozenge is defined as a hard candy, some with a glycerinated base and mucilage, and "slowly dissolving" in the mouth to release the active ingredient (Remington the Science and Practice of Pharmacy, 21st Edition, 2005, pg. 925). Menthol lozenges or cough drops typically weigh about 2.7 g (N'Ice lozenges) to 3.4 g (Walgreens cough drops) and contain from 5, 7, or 10 mg of (−)-menthol in a sugar-dye matrix. Higher doses of menthol cannot be used because it becomes irritating and unpleasant. The lozenges are held in mouth for at least 10 to 15 min, have a harsh taste, add sugar calories to the diet, but exert some cooling and soothing action on the back of the throat. Thus, a lozenge as a drug delivery vehicle, is clearly different from an ODT.

In my experience of testing an ODT containing 5 to 10 mg of (−)-menthol, I found a short cooling action, lasting less than 10 minutes. The sensation can be initially localized to the pharynx but, at higher doses of 10 mg or more, coolness rapidly extends to the upper chest, most likely as a result of the distribution of the (−)-menthol into the esophagus. This cooling sensation of the chest, felt along the sternum, can be uncomfortable. (−)-Menthol, has a smaller molecular weight than the compounds of this discovery (156 Daltons vs ~250+ Daltons), and is known to distribute rapidly away from its site of application. Menthol, because of its volatility, cannot be readily formulated into orally disintegrating tablets.

Currently available cooling agents, such as menthol and WS-3, approved for use in confectionery, do not have sufficient duration of action on the LRO to be therapeutically valuable in the treatment of cough. In order to treat cough, a compound must an anti-tussive action for at least one hour and preferably longer, otherwise the patient would have to repeatedly apply the drug to obtain relief. For an anti-irritant or anti-tussive action in the pharynx/airways, the ideal agent should have rapid onset of action, soothing effects, and the ability to relieve discomfort for an extended duration, for example, at least several hours. There must be a "wow effect" of the active ingredient to stop the cough. This is achieved by the compounds of Formula I of this discovery.

Use of NACL in Anti-Ageing and Dermatological Applications

As lifespan increases, individuals seek therapeutic procedures that allow them to cope with ageing skin. With age, wrinkles, discoloration, and changes in the growth and texture of the skin appear. Various carboxylic acids, for example, hydroxyacids and retinoic acid are topical treatments of these skin conditions. These agents achieve their effects by causing peeling of the upper skin layers. Another method of rejuvenating ageing skin is to resurface the skin with mechanical, chemical, photodynamic or laser (thermal) energy. Resurfacing the skin results in a dermal wound with associated skin discomfort. The NACL compounds may be used to alleviate the discomforts associated with skin damage caused by anti-ageing procedures and therapies.

With age, the skin is less able to retain proper moisture content. This condition, known as xerosis of the elderly, is manifested as itchy, dry, and fissured skin with scaling and sloughing. In some, xerotic skin is like cracked porcelain. The skin splits because of water loss and, if deep, disrupt capillaries and causes bleeding. Itching leads to scratching and rubbing, activities that exacerbate the pathology and produce a leather-like condition called lichenification. A provocative factor for xerosis is cold, dry weather, such as in winter or air conditioning. A study of nursing homes found xerosis and eczema was diagnosed in 29% and 37% of the patients, respectively. Therapy includes frequent application of moisturizers and steroid ointments, but will be aided by NACL compositions delivered in an ointment to relieve skin discomfort. Similarly, disorders of the skin that occur in iethycosis vulgaris and psoriasis may be so treated.

Delivery to Target and Utility of N-Alkylcarbonyl-Amino-Lactones

In formulating topical and oral compositions, the NACL compound may be incorporated into a vehicle that by itself may be inert or may contain other active ingredients.

Suitable formulations, for example, include compositions such as liquids, aerosols, powders, pastes, lotions, liniments, creams and ointments, and cosmetic preparations. A wide variety of vehicles will be suitable, depending upon the particular product involved, such vehicles including solids, liquids, emulsions, foams and gels. Typical vehicles include oils and fats such as hydrocarbon oils, polyhdric alcohols, calcium or magnesium stearate, fatty acid esters, long chain alcohols and silicone oils; finely divided solids such as starch or talc; low-boiling hydrocarbons; gums and natural or synthetic resins.

Suitable formulations for the oral cavity and oropharynx, for example, include compositions such as liquids, powders, tablets, films, or pastes. ODT, as contemplated here, are pharmaceutical dosage forms that disintegrate in saliva within 30 sec of topical application on the surface of the tongue. A typical ODT is composed predominantly of an inert vehicle, diluent, or carrier. A medicinal agent is interspersed within this carrier. The ODT will dissolve when placed on the dorsal surface of the tongue thereby releasing the medicinal agent so that it may come in contact with the tissues of the lower oropharynx (LRO). A typical diluent, carrier, or vehicle may be a "polyhydric alcohol" construed as describing the following substances: xylitol, mannitol, sorbitol, maltitol, isomaltitol, maltotriitol, lactitol, and β-linked-glucopyranasido-sorbitol. Flavoring agents such as the sweeteners, aspartame, sucralose, or alitame, may be added to mask any tastes. The mix is granulated to a uniformly dispersed blend; dispersing agents, anti-caking agents, and lubricants may be added; and the mixture is then compressed to form the ODT.

In one test formulation used in the Studies, ODT tablets were made using Ludipress®, a direct compression excipient from BASF Chemical Corp., which is a granulated blend of lactose and polyvinylpyrrolidone. The test substance was first mixed with Ludipress® using a mortar and pestle, then suspended in an equal volume of 10%-90% ethanol-distilled water (vol/vol). A disposable pipette was then used to aliquot the liquid mixture onto a sheet of wax paper and dried at room temperature. The dried tablets were then weighed and sorted. It was found by experiment that a 80 mg tablet containing 2 mg (2.5% wt/vol) of test substances dissolved within 15 seconds when placed on the dorsal surface of the tongue. A robust, refreshing cooling sensation was experienced in the LRO region that counteracted cough.

In a second formulation, the carrier was a 80%-20% mixture of mannitol-maltitol (Pearlitol™ and Sweetpearl™, Roquette Freres, France). This carrier had the advantage of completely masking bitter tastes that might be present in some of the test substances.

The duration of action of the active preparation may be further enhanced and localized at its sites of action (for example, the oropharynx) by the incorporation of mucoadhesive or bioadhesive agent. Such mucoadhesives or bioadhesives are, for example, described in U.S. Pat. No. 6,638,521 (D. J. Dobrozsi: Oral liquid mucoadhesive compositions) and U.S. Pat. No. 6,562,363 (J. Mantelle et al., Bioadhesive compositions and methods for topical administration of active agents). Typical adhesive molecules are polymers of sugars, alcohols, vinyl pyrrolidine, cellulose and the like. Dissolution of solid active ingredients in the oral cavity may sometimes be impeded by chewing or swallowing of the lozenge, or by the degree of hydration in the mouth. A liquid formulation for delivery may therefore be preferable. The NACL compounds are readily soluble (sometimes after warming) in aqueous solutions containing polyhydric alcohols, cyclodextrins, sugars and the like. These liquids, after sterilization by filtration, may be combined with preservatives, flavoring agents, solvents, and then dispensed from a reservoir type of storage container (e.g., a plastic container with a dropper type of opening) or from unit dose containers such as are readily available commercially. For example, Unicep Corporation in Sandpoint, Id., USA, has unit-dose contract packaging methods for volumes of 0.3 to 0.5 mL. A 2 to 20 mg/mL dose of a NACL compound would be an ideal form of unit dosage at these volumes of delivery. Alternatively, the NACL compound may be delivered with a nebulizer, a mouth-sprayer, or a hand-pump type of broncho-inhaler such as is well-known to those skilled in the art. In practice, the acting NACL compound may also be applied onto the skin using a towelette that is of a construction sufficient or adapted to deliver the NACL compound to the skin. Thus, the desired NACL compound is suspended, dissolved, and/or dispersed so as to be in contact with the towelette. Suitable towelettes include a pad that may be of woven or nonwoven material usually in a unit dispenser. The wiping of the towelette or pad across skin results in delivery to the skin of dermatologically active ingredient(s), meaning that the skin is substantially medicated. Other drugs, cosmeceuticals, herbal medicines, traditional medicines, and active cosmetic ingredients suitable for topical human use may also be incorporated into the towelette.

It is contemplated that the NACL compound may be incorporated into towelettes for treating the ageing skin; to treat the skin discomforts of acne, sunburn, fever, hyperthermia, fungal infections, yeast infections, rosacea, photodamaged skin; to reduce the discomforts of treatments for hyperpigmented skin, eczema, allergic or contact dermatitis, seborrheic dermatitis, mucositis, erythema, or psoriasis; and to be included with other dermatologic agents such as carboxylic acids, antibiotics, keratolytic agents or combinations thereof. In order to achieve a prolonged perfect cool, the NACL compound may also be combined with icilin, a cooling agent that acts at a molecular site that is distinct from the menthol site. Preferably, formulations are prepared with synthetic compounds that are at least 95 to 99% pure by standard analytical tests of homogeneity.

The ability of NACL compound to impart cooling and refreshment in a towelette without sting, burn or irritation (especially to the eyes), is an advance over current technology on cooling agents. Known towelettes frequently contain SD Alcohol (specially denatured alcohol; usually ethanol, isopropyl alcohol or methanol), which is present as a solvent and/or a cooling agent. Alcohol produces cooling when it abstracts heat from its environs during evaporation. The drawback of using short-chain carbon-alcohols in such formulations is that the alcohol dehydrates tissues and causes irritation. When such a towelette is used near the eyeball, the alcohol vapors irritate the eye surface. Similarly, menthol, camphor, eucalyptol, and other ingredients added to towelettes to produce fragrance and cooling also irritate the skin and eyes.

In one embodiment, a NACL compound is carried by a towelette, which, for example, when applied to the face, will be especially valuable in counter-acting fatigue and to produce alertness and increased vigilance; for example, to combat tiredness from long car journeys or work in a hot environment.

Summary of Experimental Results from Bioassays

The principal findings from experiments performed on the skin are summarized in Table 1. The beneficial effects of the NACL compounds are the long duration of action in the absence of significant eye irritation.

TABLE 1

Summary comparison of unique properties of long-acting NACL compounds with other compounds

| Chemical Class | Cooling on tongue | Cooling on skin of face | "perfect" cooling experience | Eye Irritancy | Acts for >1 hour at 40 mM |
|---|---|---|---|---|---|
| NACL | yes | yes | yes | no | yes |
| non-NACL carboxamides | yes | variable | no | yes | no |
| (−)-menthol | yes | yes | no | yes | no |
| SD alcohol | no | yes | yes | yes | no |

Synthesis of N-Alkylcarbonyl-Amino Lactones

Synthesis of the NACL compounds may be achieved by reaction of the free amine with the appropriate acid chloride, usually in the presence of a suitable acceptor for hydrogen chloride, which could be an excess of the free amine or another base, e.g., triethylamine.

The reaction is typically carried out in a suitable organic solvent, but, depending on the reactivity of the acid chloride, may also be carried out in a mixed aqueous/organic solvent system, in which case a convenient base is sodium bicarbonate.

Such methods of adjusting the reaction to encourage conversion and/or to avoid certain impurities are well known to those skilled in the art.

Many reagents used here may be obtained from commercial sources such Sigma-Aldrich Corp., St. Louis, Mo., USA. For example, R- or S-, or R/S amino butyrolactone are listed in the 2003-2004 Aldrich Catalog. The acid chloride is reacted with the appropriate amino acid ester to form the NACL compound.

Synthesis of 2-Isopropyl-5-methyl-cyclohexanecarbonyl-L-Hsl (also known as: (1R,2S,5R)-2-isopropyl-5-methyl-cyclohexanecarboxylic acid (S)-(2-oxo-tetrahydro-furan-3-4-amide)

(S)-α-amino-γ-butyrolactone hydrochloride was obtained from Aldrich Chemical Co., 500 mg was dissolved in 18 mL diethyether and 1.5 mL double-distilled water. A pinch of the catalyst diaminopyrimidine was added. 0.68 mL of p-menthoyl chloride was then added dropwise, followed by 1.02 mL of triethylamine. The mixture was stirred overnight at room temperature. The precipitate was dissolved with ethyacetate, washed with double-distilled water and dried over sodium sulfate. The organic phase was then evaporated under reduced pressure to yield the final product, which crystallized at room temperature. The expected molecular mass was then confirmed by mass spectroscopy and the absorption spectrum by nuclear magnetic resonance.

Bioassay Procedures

The NACL compounds are white crystalline solids at room temperature. For bioassay on the skin, approximately 30 mg was stirred and dissolved in 3 g of warm liquid Aquaphor® ointment to a yield a ~1% wt/vol ointment. After cooling, 40 to 70 mg of the solid ointment was placed on the tip of a plastic stick and applied to the skin above the upper lip, on the philtrum, and lateral to the philtrum, up to the nasolabial folds, of test subjects and the onset and duration of cooling sensations noted.

The intensity of the subjective skin sensation was rated as 0, 1, 2 or 3 with: 0 as no change; 1 as slight coolness, cold, or tingling; 2 as clear signal of coolness, cold, or tingling; and 3 as robust cooling or cold. The intervals for recording sensations were 5 to 10 minutes, until two successive zeroes were obtained. The results (shown in FIG. 1) are averaged values of 4 to 6 separate trials in the same individual. The data are plotted using SigmaPlot® (Systat Software, Point Richmond, Calif., USA) and a smoothing function with a negative exponential was used for analysis and statistical fit of the results.

For tests of irritancy near the eyes, the ointment was applied to the periorbital skin (upper and lower eyelids and on skin adjacent to the lateral canthus), and the subject asked if irritation is present or absent. The intensity of the eye sensation is not rated, but just noted as being present or absent.

The onset of drug action was taken as the time to reach 2 units of coolness intensity, and offset of drug action was the time when coolness intensity drops below 2, after previously surpassing 2 units. The duration of cooling action was defined as the offset time minus the onset time. An inactive compound is defined as one that did not exceed 2 units of cooling after application. The quality of the sensation was also noted: such as pure refreshing coolness, or if the sensation was accompanied by irritation (stinging or burning). The quality of the sensation was not rated for intensity.

It has been found that the most effective method for testing a compound for effects in the oral cavity is to take a 1 to 5 mg sample and place it on the dorsal surface of the tongue, ⅔ posterior from the tip and in the midline. The subject is instructed to close and hold the substance in the mouth for at least 10 seconds and not to swallow. The description of sensations is then recorded at 5 to 10 minute intervals.

Anti-Cough Activity A number of cough challenge methods have been devised for evoking the cough reflex (Morice et al. Briti. J. Clin. Pharmacol. 52: 365-375, 2001). Usually, citric acid or capsaicin is delivered via the inhalation route to volunteers and the number of coughs counted. I have found that the sensations in the lower pharynx associated with the urge to cough can be replicated by placing (with a syringe or a plastic stick) 0.2 to 0.25 ml of a chili pepper sauce onto the posterior dorsal surface of the tongue. The chili pepper sauce used here is called Yank Sing® Chili Pepper Sauce (YS Gourmet Productions, Inc., PO Box 26189, San Francisco, Calif. 94126) and is a well-known condiment for use with dim sum (Chinese tea lunch). The sensations associated with the chili pepper sauce are located in the back of the mouth and are clearly recognized and associated with a desire to clear the throat.

The chili-pepper sauce evoked sensations can be readily suppressed with a drink of ice cold water or with an ODT containing a cooling ingredient, but is not affected by an ODT containing only the excipient. To test for anti-cough activity the ODT with the test substance is first administered onto the dorsal surface of the tongue and 45 to 50 min afterwards the chili-pepper sauce test is administered. If there is no attenuation of the challenge stimuli, the score is 0, if there is partial inhibition, the score is +, and if there is complete attenuation of the cough signal, the score is ++. In the presence of an ODT that results in a ++ score, the irritative signals are completely absent, yet the salty taste used in the soy sauce of the condiment can still be easily tasted. The test substances in the ODT that produced a ++ score were then identified and further tested for effectiveness in the treatment of cough.

To further document the activities of the test molecules, the results from an eye wipe test was included. Here the test substance is applied to the closed eyelids with a towelette at a concentration of 1 mg/ml in 5%-ethanol-95%-distilled water vol/vol and the duration of cooling on the ocular surface was recorded. Surprisingly, a good correlation was found between ocular cooling duration and anti-cough activity and less so with the duration of cooling based on the philtrum skin assay. It is likely that the mucous membranes that line the ocular surface and the pharynx have similar sensory mechanisms that are somewhat different from the philtrum skin which is keratinized.

Study 1

A number of compounds were synthesized and tested with the results are shown in FIG. 1 and the Tables. Test compounds were singly applied to the skin above the upper lips at 5 mg/ml or ~10 mg/ml (40 mM) ointment.

FIG. 1 is a graph showing duration of cooling (hours) for six compounds (in order, left to right): WS-3, WS-23, (−)-menthol, WS-5, D-Hsl, and L-Hsl. The durations of cooling effects of known agents, e.g., (−)-menthol, WS-3, WS-23 and WS-5 are ≦0.5 hr. By contrast, L-Hsl, D-Hsl, and racemic Hsl (Table 2) act for 1.3, 1.3 and 1.4 hours, respectively. WS-12, a potent activator of TRP-M8 receptors, is not on the skin (0.4 hr, Table 5). The presence the lactone ring in D-Hsl increases duration of action and these compounds are examples of the preferred embodiments of this invention.

The NACL derivatives produced a refreshing cool, without irritancy, when applied on the skin or on the ocular surface. As an ODT, the Hsl analogs produced a refreshing perfect cool in the oral cavity and on the pharyngeal surface. The effective dose in the oral cavity was 2 to 5 mg, and the cooling action lasted from 15 to 30 min. When formulated as an ODT, the Hsl analogs, especially D-Hsl, is effective in the treatment of cough. Thus, the Hsl analogs have special utility and are embodiments of this discovery.

The data in Table 2 and 3 and in FIG. 1 show that the NACL have increased potency and duration of action relative to other cooling congeners. Also, these lactone analogs have the property of producing a selective refreshing coolness with the absence of tissue irritation when applied to the skin, ocular surface, and to the pharyngeal surface.

One unusual feature noted in the pepper-sauce assay and the use of ODT on cough in human subjects is that the cooling action on the oropharynx lasts about 10 to 15 min, yet the antitussive effects lasts for 3 or more hours. This action can be explained if it is clearly recognized that the antitussive action is indirect, acting via a gating mechanism. There is no direct drug action of the cooling agent on the cough receptors. It is the Aδ-fiber transmitted signal that is triggering release on an inhibitory mediator (perhaps via metabotropic Glu receptors) that is gating the cough signal. The gating mechanism in the central nervous system may desensitize, hyper-polarize, or otherwise modulate the sensitivity of central neurons for an extended period of time. That is, there is a lingering memory trace in the brain that attenuates the sensations of and/or the urge the cough.

To describe this idea in lay terms, I use the analogy of going out into the spring sunshine for 15 min, being happy, and then coming back indoors. Although the skin is no longer warm after leaving the sun, the change in mood may last for several hours or longer. A pleasant cooling memory trace may thus reduce sensitivity to noxious stimuli (Wordsworth: "They flash upon that inward eye, Which is the bliss of solitude; And then my heart with pleasure fills, And dances with the daffodils.")

TABLE 2

Active compounds of this invention. Philtrum assay using 10 mg/ml of test substance in ointment.

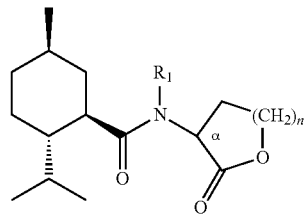

Formula (1)

| Compounds | $R_1$ | n | Duration of Action On-Off (minutes) |
|---|---|---|---|
| D-Hsl (no. 1, *) | H | 1 | 2 to 80 = 78 |
| L-Hsl (no. 2, *) | H | 1 | 2 to 87 = 85 |
| racemic Hsl (no. 3, *) | H | 1 | 2 to 86 = 84 |

The no. refers the structure as shown in Table 1. (*) denotes compounds with refreshing cooling and absence of skin irritation or eye irritation after facial skin or periorbital applications; a "perfect cool" Hsl=homoserine lactone (also known as α-amino-butyro-γ-lactone))

TABLE 3

Bioassay results of various compounds. Substances were tested in philtrum assay using 5 mg/ml ointment. The eye wipe tests were with a towelette containing 1 mg/ml of substance in 5%-95% v/v ethanol-distilled water. The duration of cooling is recorded as (minutes). For the chili pepper sauce test if there is no attenuation of the challenge stimuli, the score is 0, if there is partial inhibition, the score is +, and if there is complete attenuation of the cough signals, the score is ++.

| Compounds | $R_1$ | $R_2$ | Philtrum Skin (min) | Eyelids/ Ocular Surface (min) | Chili-Pepper Sauce Test |
|---|---|---|---|---|---|
| Gly-OEt (WS-5) | H | Et | 24 | 15 | 0 |
| Gly-OnPr | H | nPr | 42 | 54 | 0 |
| Gly-OnBu | H | nBu | 38 | 35 | 0 |
| L-Ala-OEt | Me | Et | 34 | 0 | 0 |
| D-NMeAla-OEt | Me | Me | 0 | 0 | 0 |
| D-Hsl (*), structure as in table 2 | | | 65 | 110 | ++ |
| L-Hsl (*), structure as in table 2 | | | 72 | 120 | ++ |
| D/L Hsl (*), structure as in table 2 | | | 70 | 125 | ++ |

(*) denotes compounds that fulfill the criteria of being a long-acting NACL for skin, ocular surface, and anti-cough applications (i.e., ≧1 hour duration of action).

TABLE 4

Compounds described by Watson et al. that were tested on the philtrum skin assay using 10 mg/ml of test substance in ointment.

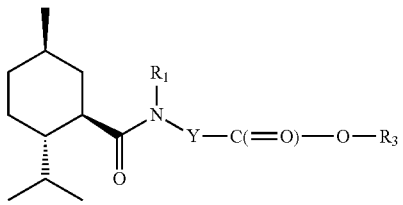

| Compounds | $R_1$ | Y | $R_3$ | Duration of Action On-Off (minutes) |
|---|---|---|---|---|
| Gly Me Ester (WS-31) | H | —$CH_2$— | Me | 5 to 25 = 20 |
| Gly Et Ester (WS-5) | H | —$CH_2$— | Et | 4 to 37 = 33 |

Examples of N-alkyl- or aryl-cycloalkyl carboxamides that are inactive or are only briefly cooling on philtrum skin [tested ~10 mg/ml (40 mM)] are shown in Table 4 to 7.

TABLE 5

Compounds described by Watson et al. that were tested on the philtrum skin assay using 10 mg/ml of test substance in ointment.

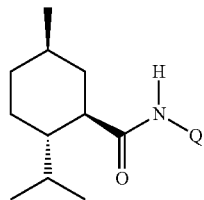

| Compound | Q | Duration of Action On-Off (minutes) |
|---|---|---|
| WS-3 | ethyl, —$CH_2CH_3$ | 5 to 23 = 18 |
| WS-10 | isopropyl, —$CH(CH_3)_2$ | 6 to 25 = 19 |
| WS-34 | sec-butyl, —$CH(CH_3)CH_2CH_3$ | inactive |
| WS-14 | t-butyl, —$C(CH_3)_3$ | 15 to 23 = 8 |
| WS-11 | 1',1'-dimethyl-2'-hydroxyethyl, —$C(CH_3)_2CH_2OH$ | 8 to 18 = 10 |
| WS-12 | 4'-methoxyphenyl, —$C_6H_5$-4'-OMe | 13 to 38 = 25 |

TABLE 6

Compounds found to be Inactive when they were tested on the philtrum skin assay using 10 mg/ml of test substance in ointment.

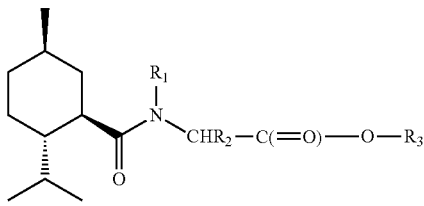

| Compounds | $R_1$ | $R_2$ | $R_3$ | Duration of Action On-Off (minutes) |
|---|---|---|---|---|
| Ser Et Ester | —H | —$CH_2$—OH | Et | not active |
| Glu(OMe) Me Ester | —H | —$(CH_2)_2$—C(=O)—OMe | Me | not active |
| Lys(Z) t-Bu Ester | —H | —$(CH_2)_4$—NH—C(=O)—O—$CH_2$—$C_6H_5$ | t-Bu | not active |

TABLE 6-continued

Compounds found to be Inactive when they were tested on the philtrum skin assay using 10 mg/ml of test substance in ointment.

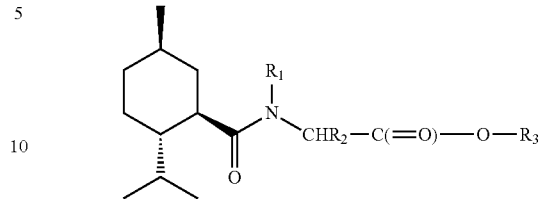

| Compounds | $R_1$ | $R_2$ | $R_3$ | Duration of Action On-Off (minutes) |
|---|---|---|---|---|
| Tyr Me Ester | —H | —$CH_2$—$C_6H_4$-4'-OH | Me | not active |
| L-Val Me Ester | —H | —CH—$(CH_3)_2$ | Me | not active |
| D-Val Me Ester | —H | —CH—$(CH_3)_2$ | Me | not active |
| Leu Me Ester | —H | —$(CH_2)_2$—CH—$(CH_3)_2$ | Me | not active |

(Ser = serine; Glu = glutamic acid; Lys = lysine; Tyr = tyrosine; Val = valine; Leu = leucine.)

TABLE 7

Compounds found to be Inactive when they were tested on the philtrum skin assay using 10 mg/ml of test substance in ointment.

| Compound | Structure | Duration of Action On-Off (minutes) |
|---|---|---|
| Pro Me Ester | 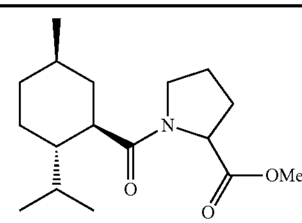 | not active |

Study 2

Physical Properties and Tongue Thresholds for Cooling of Various Compounds

The octanol/water partition coefficients (given in log P units) for a number of compounds were determined and are shown in Table 8, together with the threshold for cooling on the tongue, as reported previously by the WS patents. As can be seen from this data, there is no correlation between tongue cooling and the duration of cooling. A longer duration of action was not precisely matched with log P values.

TABLE 8

Some properties of tested compounds. The tongue threshold values are from Watson US 04178459.

| Compound | Molecular Weight | Threshold tongue (µg) | Log P |
|---|---|---|---|
| Gly Me Ester (WS-31) | 255.4 | 0.6 | 2.4 |
| Gly Et Ester (WS-5) | 269.4 | 0.2 | 2.9 |
| Gly n-Pr Ester | 283.4 | 0.3 | 3.4 |
| Gly n-Bu Ester | 297.4 | — | 4.0 |
| Sar Et Ester | 283.4 | 0.8 | 2.9 |
| L-Ala Et Ester | 283.4 | 0.4 | 3.1 |
| L-Ala Me Ester | 269.4 | 0.6 | 2.8 |
| N-Me-D-Ala Et Ester | 297.4 | — | 3.2 |
| β-Ala Et Ester | 283.4 | 1.5 | 3.1 |

TABLE 8-continued

Some properties of tested compounds.
The tongue threshold values
are from Watson US 04178459.

| Compound | Molecular Weight | Threshold tongue (μg) | Log P |
|---|---|---|---|
| D-Hsl (*) | 267.4 | — | 2.5 |
| L-Hsl (*) | 267.4 | — | 2.5 |
| racemic Hsl (*) | 267.4 | — | 2.5 |
| WS-3 | 211.3 | 0.2 | 3.7 |
| WS-10 | 225.4 | 0.4 | 4.1 |
| WS-34 | 239.4 | 0.7 | 4.6 |
| WS-14 | 239.4 | 0.4 | 4.5 |
| WS-11 | 255.4 | 0.3 | 2.9 |
| WS-12 | 289.4 | 0.2 | 5.3 |
| L-Ser Et Ester | 285.4 | — | 1.8 |
| L-Val Me Ester | 297.4 | — | 4.2 |
| D-Val Me Ester | 297.4 | — | 4.2 |
| Glu(OMe) Me Ester | 341.4 | — | 2.2 |
| L-Leu Me Ester | 311.5 | — | 4.3 |
| L-Pro Me Ester | 295.4 | — | 3.3 |
| L-Lys(Z) t-Bu Ester | 502.7 | — | 5.9 |
| L-Tyr Me Ester | 364.2 | — | 3.7 |

Study 3

The compounds of Formula (1) are white crystalline solids at room temperatures. D-, L-, and racemic Hsl analogs falling within Formula (1) ((1R,2S,5R)-2-isopropyl-5-methyl-cyclohexanecarboxylic acid (R/S)-(2-oxo-tetrahydro-furan-3-yl)-amide) were tested at 2 to 5 mg per dose as an ODT formulation. These compounds produced robust and prolonged cooling at the back of the throat. The potent topical activities of the lactone NACL on bioassay endpoints were unexpected as there is no a priori reasons to assume the lactone ring resulting from cyclization of the alkylester to the α-carbon will allow the molecules to retain and sustain its biological cooling actions.

For compounds of Formula (1), the α-carbon may independently be in the D-amino acid configuration (i.e., (R)-configuration) or the L-amino acid configuration (i.e., (S)-configuration. Both enantiomers, and (e.g., racemic) mixtures thereof, are approximately equipotent in biological terms. The chiral center of the lactone is such that there may be no significant energy barriers in assuming either of the active configurations. Thus, a racemic mixture of the lactone may also be useful.

The L-homoserine lactone, (1R,2S,5R)-2-isopropyl-5-methyl-cyclohexane carboxylic acid (S)-(2-oxo-tetrahydro-furan-3-yl)-amide (an analog of compounds of Formula (1)), bears some resemblance to the N-acylhomoserine lactone family of molecules secreted by Gram-negative bacteria. These "quorum-sensing" signal molecules constitute one of the few mechanisms by which bacteria can communicate with each other. Although not fitting the exact structural requirements for quorum-sensing activity, it is likely that the L-homoserine lactone analog will face severe toxicology scrutiny for pharmaceutical applications.

The D-homoserine lactone does not possess quorum-sensing activity but the D-Hsl starting material is likely to be expensive for manufacture of the final product in bulk quantities. Thus, the D-homoserine lactone compound, (1R,2S,5R)-2-isopropyl-5-methyl-cyclohexane carboxylic acid (R)-(2-oxo-tetrahydro-furan-3-yl)-amide (an analog of compounds of Formula (1)) may be used as a cough inhibitor, but it is more expensive than the compounds of Formula (1).

Study 4

A 62-year female was cooking spaghetti for a party of ten when she accidentally touched the volar surface of her right forearm against a large pot full of boiling water. A 2.5 inch red wheal developed quickly at the site of contact and the subject complained of sharp pain. A 1% wt/vol ointment of o-Hsl (no. 1 in Table A) in Aquaphor® was applied to the wheal and to the adjacent skin (~3 in diameter circle), using a plastic stick. The subject remarked that the "edge" of the pain disappeared within 5 min and she felt much better. However, ~40 min later the pain returned. The ointment was again applied, only this time to a larger area (~5 inch diameter circle) around the site of injury. The pain disappeared completely and the subject noted that the redness and swelling was also reduced. The subject "forgot" about the injury and participated actively in the party. Next day, she noticed that there was a faint pink-colored spot at the site of the injury but no swelling. There was no irritation or pain.

Study 5

ODT containing 2.0 to 2.5 mg of D-Hsl (identified as no. 1 in Table A) were prepared using mannitol/maltitol as the excipient and stored in tic-tac boxes each containing 10 tablets. Over a course of two years, 6 adult males with cough tested these tablets. The causes of coughing were colds/flu, allergies, pharyngitis, and excessive smoking. These individuals all had advanced degrees (M.D. or Ph.D.) and were motivated to try the tablets by scientific curiosity or because of financial interests in drug development, or, in several cases, by the annoyance caused by the cough. These subjects had no difficulties in learning how to self-administer the ODT. The ODT placed on the mid-posterior dorsal surface of the tongue disintegrated in saliva in less than 15 sec and the sensory agent was then felt to coat the lower pharynx. No adverse effects were noted. Placebo ODT containing the excipient alone or the D-NMe Ala Ester or L-Ala Et Ester were immediately detected as being inactive and thereby rejected after one trial. The ODT containing D-Hsl was 100% effective in reducing cough. The desired pharmacological effect was achieved in all subjects. The individual not only felt better, but the people around the subjects within 10 min noticed the absence of coughing after administration. There was no ambiguity about the ability of the D-Hsl ODT to reduce coughing and to counteract pharyngeal irritation in all tested subjects.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. A compound having the structure of Formula (1):

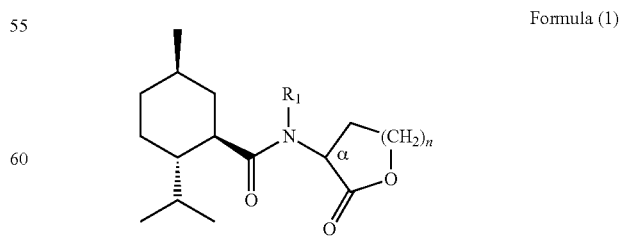

Formula (1)

wherein:

n and $R_1$ hydrogen.

2. The compound according to claim 1, which is (1R,2S,5R)-2-isopropyl-5-methyl-cyclohexanecarboxylic acid ((S)-2-oxo-tetrahydro-furan-3-yl)-amide.

3. The compound according to claim 1, which is (1R,2S,5R)-2-isopropyl-5-methyl-cyclohexanecarboxylic acid ((R)-2-oxo-tetrahydro-furan-3-yl)-amide.

4. The compound according to claim 1 which is (1R,2S,5R)-2-isopropyl-5-methyl-cyclohexanecarboxylic acid ((R/S)2-oxo-tetrahydro-furan-3-yl)-amide.

5. A composition comprising a compound of claim 1.

6. The composition according to claim 5, wherein the compound is present in the composition in an amount of 0.1 to 5% wt/vol.

7. The composition according to claim 5, wherein the composition further comprises one or both of a polyhydric alcohol and a mucoadhesive polymer.

* * * * *